United States Patent [19]

Gruner et al.

[11] Patent Number: 4,458,155
[45] Date of Patent: Jul. 3, 1984

[54] DEVICE FOR INSPECTING A CASTING

[75] Inventors: Hans Gruner, Duisburg; Hans Schrewe, Düsseldorf; Fritz-Peter Pleschwtschnigg, Duisburg; Jothar Parschat, Essen, all of Fed. Rep. of Germany

[73] Assignee: Mannesmann AG, Duesseldorf, Fed. Rep. of Germany

[21] Appl. No.: 337,622

[22] Filed: Jan. 7, 1982

[30] Foreign Application Priority Data

Jan. 12, 1981 [EP] European Pat. Off. ........ 81730005.6

[51] Int. Cl.³ .................... G01N 21/32; H04N 7/18
[52] U.S. Cl. ............................ 250/572; 358/106; 356/431; 250/341
[58] Field of Search ............. 250/341, 572, 223 B, 250/238, 554, 575, 563; 358/106

[56] References Cited

U.S. PATENT DOCUMENTS 4,020,949  5/1977  Erdman .................. 250/223 B
4,328,488  5/1982  Yhnai et al. ............. 250/554

Primary Examiner—David C. Nelms
Assistant Examiner—Ernest Austin, II
Attorney, Agent, or Firm—Ralf H. Siegemund

[57] ABSTRACT

A hot casting, freshly emerging from the mold, is inspected for any surface defects by a revolving line scan camera; the camera is disposed in an annular water-cooled, two-part housing having an inwardly directed annular gap covered by a sheet that revolves with the camera; the camera can look through a small gap of that sheet.

12 Claims, 8 Drawing Figures

Fig.5
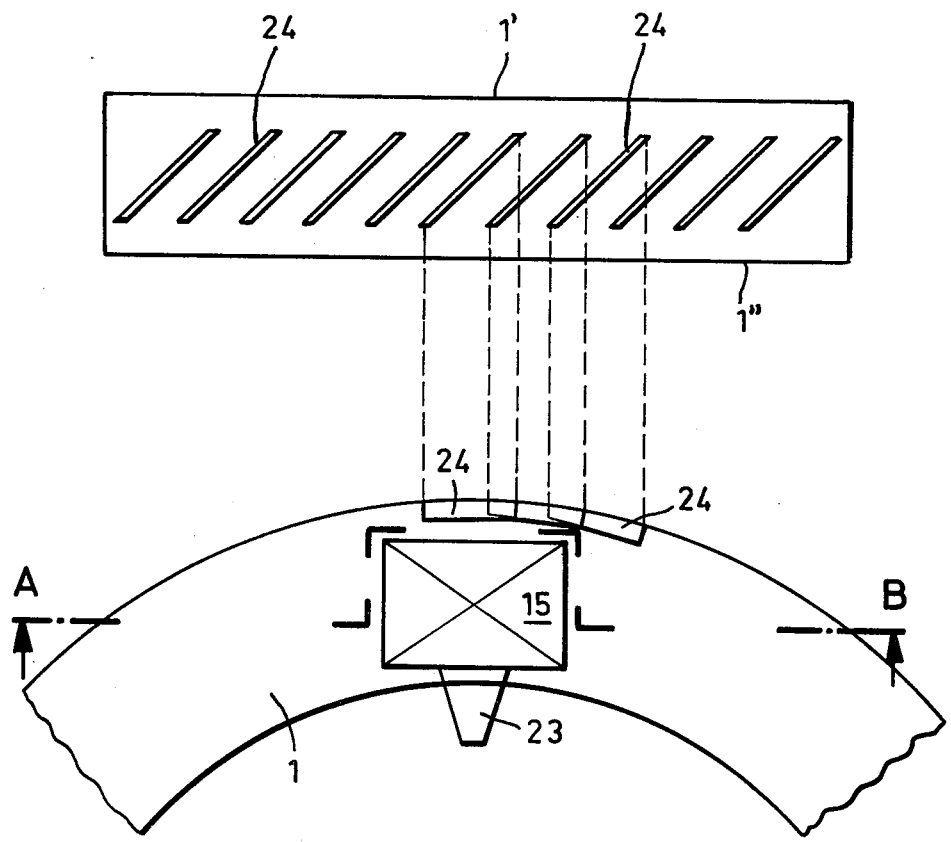
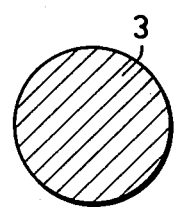

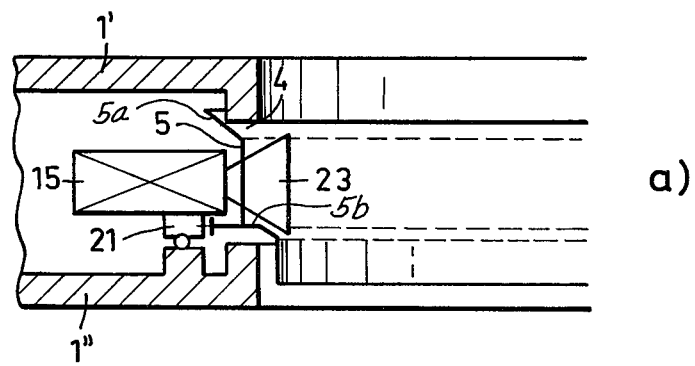
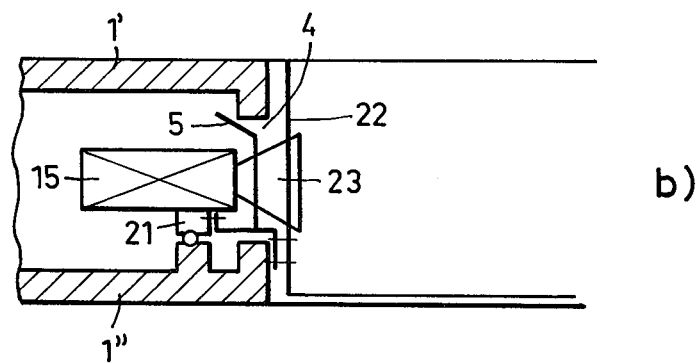
Fig.6
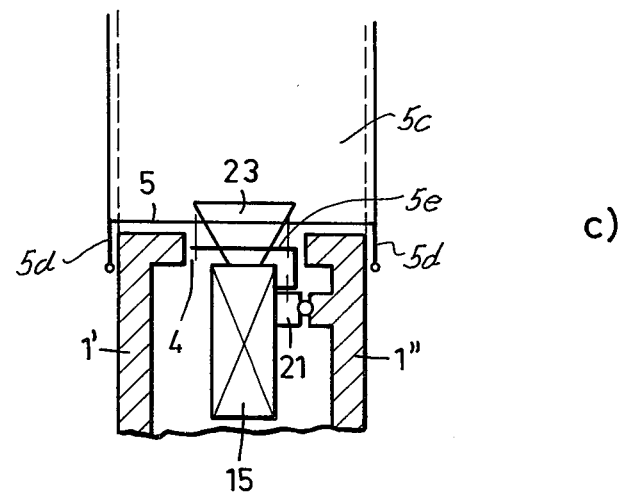

DEVICE FOR INSPECTING A CASTING

BACKGROUND OF THE INVENTION

The present invention relates to the direct inspection of castings as they emerge from a machine for continuous casting, such an inspection to be carried out under conditions of exposure of heat emanating from the barely solidifying casting.

In the past, visual inspection of a casting by experienced personnel has been the common practice. The same is true with regard to solidified casting ingots; however, other inspection methods of cold ingots involve utilization of ultrasonics, magnetic fields as they are varied by defects, chemical effects, or other metal checks. Not only does the ingot so inspected have to be cold (relatively speaking, the temperature should be lower than approximately 300° C.), but the test piece should be stationary.

German printed patent application No. 29 11 578 discloses a system for optical inspection of a casting, using a supplemental light source and detecting particular reflection features which can be attributed to surface defects.

DESCRIPTION OF THE INVENTION

It is an object of the present invention to detect surface features of a casting for purposes of early recognition of surface defects, under consideration of the surface geometry. The detection equipment should be amenable to inspection of castings of different diameters and different cross sections.

It is a feature of the present invention to directly utilize the thermal radiation that emanates from a casting, and it is a related feature that a line scan camera e.g. a linear array of radiation-sensitive diodes be used responding e.g. to radiation that emanates at temperatures of higher than 500° C.

In accordance with the preferred embodiment of the present invention, an annular or ring-shaped housing surrounds the casting; and its wall which faces the casting is provided with an annular gap; the gap is covered with suitable sheet means which revolve about the common axis. The sheet itself has a narrow gap behind which is located the line scan camera. Sheet and camera are driven in order to revolve inside the housing about their common axis to thereby inspect the surface of the casting along a, basically, helical scanning band. The housing is water-cooled, whereby for reasons of safety several independant water-cooling systems are employed. The tubing for the cooling system actually establishes the houses.

The housing is of a two-part configuration, the gap does separate the two parts. Preferably, the lower one has a U-shaped profile, the upper part is annularly flat and covers the U. Oblique lamellas should be provided in the housing, penetrating into its interior to the extent permitted by the revolving camera in order to provide a more uniform temperature in the housing.

A counterweight may be provided opposite the camera, along a diagonal line. However, one may even provide here a second camera, whereby the two scanning lines are inclined to each other at a 90° angle, each line being oblique to the central axis. In other words, the two scanning-line arrays operate along orthogonal scanning lines. This permits each scan to traverse any defect boundary from different directions so that a defect will certainly be scanned at least once, more or less transverse to its boundaries!

The revolving speed, length of the scanning strip for each line, and the speed of the casting should be selected so that adjacent "loops" of the scanning band overlap by at least 5%, possibly even as much as 50%, in order to obtain some redundancy for reason of certainty of detection. In the case of a square-shaped casting, care must be taken that the resolution of inspection does not suffer on account of the variation in a relative scanning angle. This, in effect, limits the scanning speed.

DESCRIPTION OF THE DRAWINGS

While the specification concludes with claims, particularly pointing out and distinctly claiming the subject matter which is regarded as the invention, it is believed that the invention, the objects and features of the invention, and further objects, features and advantages thereof, will be better understood from the following description taken in connection with the accompanying drawings, in which:

FIG. 5a is a similar view but for a round casting and showing certain details;

FIG. 5b is a section view along line A and B in FIG. 5a; and

FIGS. 6a, 6b, and 6c are cross sections of three different sheet profiles covering the housing gap that faces the casting.

Proceeding now to the detailed description of the drawings, FIG. 1 shows a casting ladle 16 cooperating with a tundish 17 serving as a buffer and distributor; particularly, for pouring molten steel at a regular rate into a mold 18. The mold may be of a curved configuration so that a curved casting 3 is formed directly and emerges from the open bottom of the mold. Support and withdrawal rolls 19 veer the casting into the horizontal. The frame and stand and other supporting equipment are sketched in only because they are quite conventional.

Reference numeral 20 refers to the inventive inspection equipment. It was found suitable to place it just ahead of the horizontal casting path. The station 20 is obliquely oriented as the casting is to traverse the plane of extension of station 20 at right angles. Thus, the orientation of casting 3 in the vertical, as per FIG. 2, is for purposes of illustration only, and it is understood that the true vertical in FIG. 2 would point into the 2-o'clock position.

Figure 1:
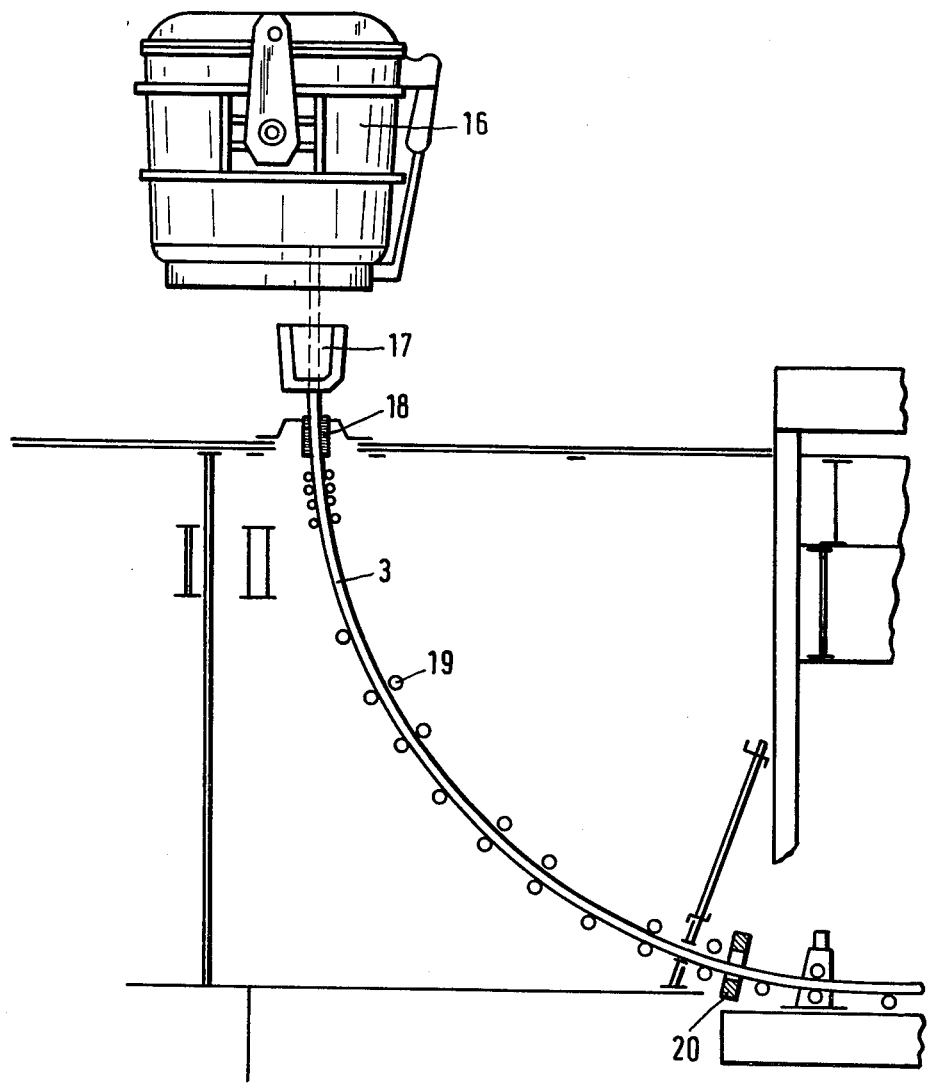
FIG. 1 is a schematic overview of a machine for continuous casting, improved in accordance with the preferred embodiment of the invention for practicing the best mode thereof.
Figure 2:
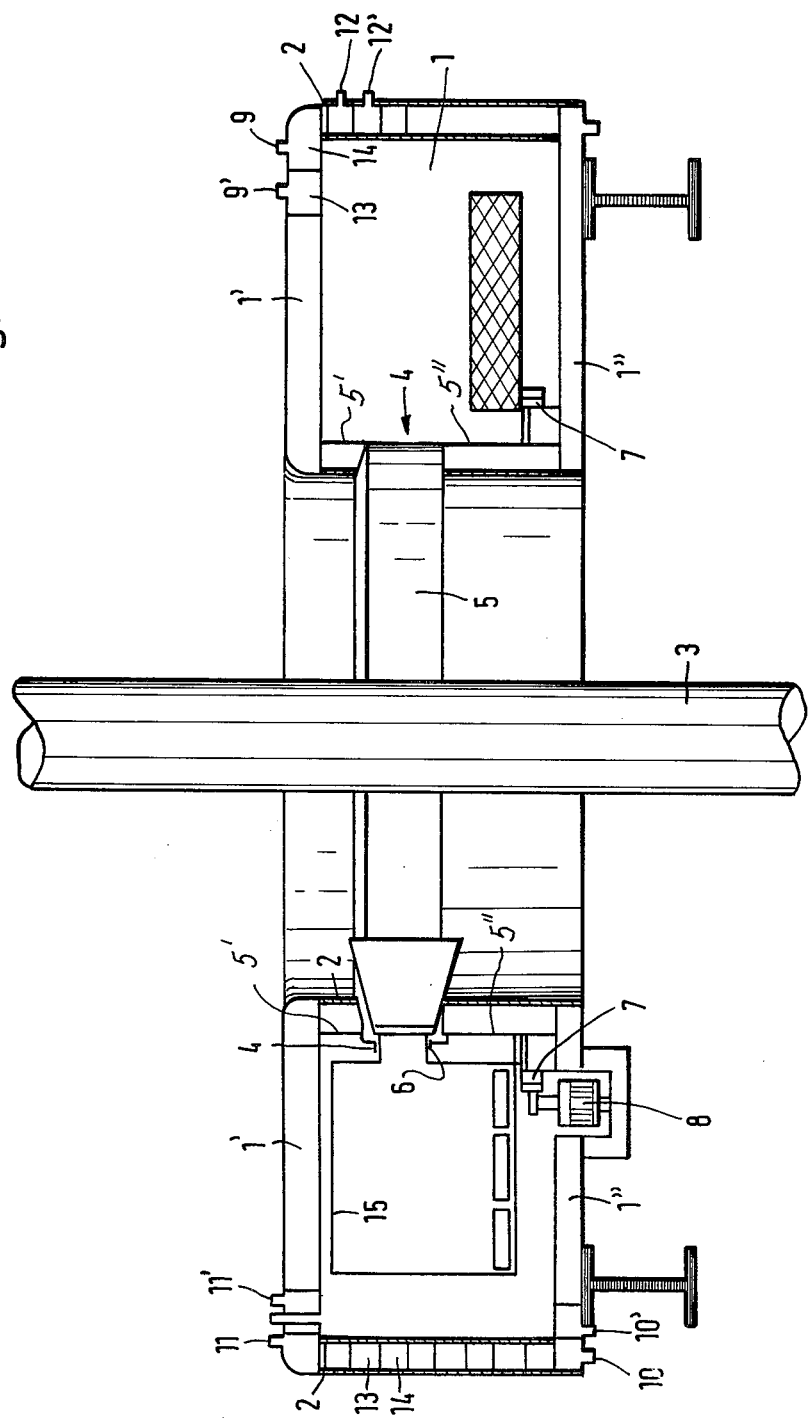
FIG. 2 is a cross section through a first example of the preferred embodiment as applied for inspecting a round casting.

On the other hand, it should be noted that the preferred mode of practicing the invention is to place the inspection station as close to the mold as possible because early recognition of surface defects may permit intervention in the casting process for avoiding the production of long defective castings. It is believed, at this time, that the inspection equipment can be shifted somewhat upward, but steam development of extensive external surface cooling is an impediment against optical type of inspection.

The casting 3 is surrounded by a ring-shaped housing 1, which is comprised of two parts (1' and 1") and includes a water-cooling system. Tubes 13 and 14 of rectangular cross sections run around and in the outer periphery of the housing parts to establish several cooling systems. Upper and lower housing parts do each have two cooling systems, whereby the tubes of the respective two systems are tightly interconnected and welded. In fact, these welded-together systems of tubings establish by themselves the housing parts.

The upper housing part 1' has two water inlets 9 and 9' for its two cooling systems, and there are two corresponding outlets 11 and 11' in diametrically opposed positions. The lower housing part 1" has correspondingly two inlets 12 and 12' for its two cooling systems, there being two outlets 10 and 10' accordingly. It can be seen that the two particularly identified tubes (13 and 14) pertain to different cooling systems for housing part 1".

The two housing parts are physically separated in a center joint 2 which, however, is closed, and in an inner joint which is constructed as a rather wide annular gap 4. One can also say that the inwardly directed wall of the enclosure has this annular gap facing concentrically casting 3.

This annular gap 4 is closed (except, where stated below) by an annular sheet having flange portions 5' and 5". This sheet 5 can be shifted, i.e., it may revolve about the central axis of the ring-shaped housing construction. Sheet 5 has a narrow gap 6, having its long dimension extend parallel to the direction of casting i.e., of movement of casting 3. A camera 15 is provided to observe and inspect the casting through that narrow gap.

FIG. 6 shows other versions and modifications of the sheet 5. Generally speaking, this sheet protects the interior of the housing against heat, water, and dirt. The sheet 5 is, in addition, provided with an annular ring gear 7, and a pinion on a shaft of a motor 8 engages that gear, causing sheet and camera to rotate on the central axis so that the camera is progressively oriented toward different portions of the casting 3. The motor 8 should be controlled toward a constant speed, selected as will be described more fully below. The drive is preferably an electric one, but a hydraulic drive or a pneumatic drive may be used instead. In either case, the drive should be stationary.

In FIG. 6a, the sheet has an upward flaring portion 5a and a downward extension 5b. Thus, the sheet portion 5a extends on the inside of housing part 1' and portion 5b extends generally on the inner outside of housing part 1"; the major portion of the sheet extends in approximately the middle of gap 4. Portion 5b includes a radially inward-angled and downward-flaring part from which a cylindrical portion extends to run adjacent to the inner wall of housing part 1".

The particular sheet is releasably fastened to a rotatable frame 21 which is articulated on an annular rail of the housing part 1" in a manner that permits the frame to run on this circular rail track while the camera can be swiveled up or down for proper orientation. The camera 15 is likewise affixed to frame 21 and can be turned on the center axis of the system in order to inspect casting 3 from all sides, through the gap 6 in sheet 5, as was described with reference to drive 8. Thus, the sheet 5 is, in all these instances, provided with an annular gear track.

The sheet 5 is slightly differently contoured in the example of FIG. 6b. Moreover, a shield 22 (with a narrow gap for the optical camera input) is provided in front of sheet 5, on the inside of the central space defined by the ring-shaped housing. This shield offers additional heat protection, particularly against the still rather intense thermal radiation that emanates from the casting 3.

The particular shield structure of FIGS. 6a and 6b are suitable mostly for a disposition of the inspection station along a more vertical portion of the casting;

FIG. 6c shows a configuration that is preferred for a disposition along a more horizontal portion of the casting (such as in FIG. 1). In this particular case, sheet 5c actually covers the entire outside of the radially inward-oriented wall of the housing and has additional, radial, outward flange extensions 5d. A second portion of this shielding arrangement (5e) runs in gap 4.

In all versions, a funnel-shaped element 23 in front of camera 15 is directed toward the casting and provides additional protection for the camera.

FIGS. 5a and 5b illustrate additionally lamellas 24 as being arranged along the outer inside wall of housing portion 1". The lamellas extend close to the track path of camera 15. These lamellas extend the effect of cooling much into the housing interior as possible.

After having described the equipment as to its general layout, reference is made first to the camera 15. This camera is a vertical line scan camera, having as an optical input element, for instance, a vertically oriented linear array of diodes which are sequentially electronically scanned. This way, a particular portion of casting 3 is monitored in each instance. Assuming the camera to be stationary, then an axial strip will be progressively scanned with each run, the width of the strip depending upon the area monitored by each diode in the said array. The azimuthal width of that strip being scanned as well as its axial length depend also upon the optics of the camera.

If the camera rotates, that strip being scanned in one scanning run assumes a slightly oblique position on the moving casting; and upon rotation of the camera under continuous repetition of the line scan, that strip develops into a helical scanning band. Clearly, the (axial) progression of the casting through the equipment should be such that, upon one complete revolution of the camera, the casting has progressed by not more (preferably less) than the axial length of the scanning strip. The helical band overlap should be at least 5%, possibly as much as 50%.

Figure 3:
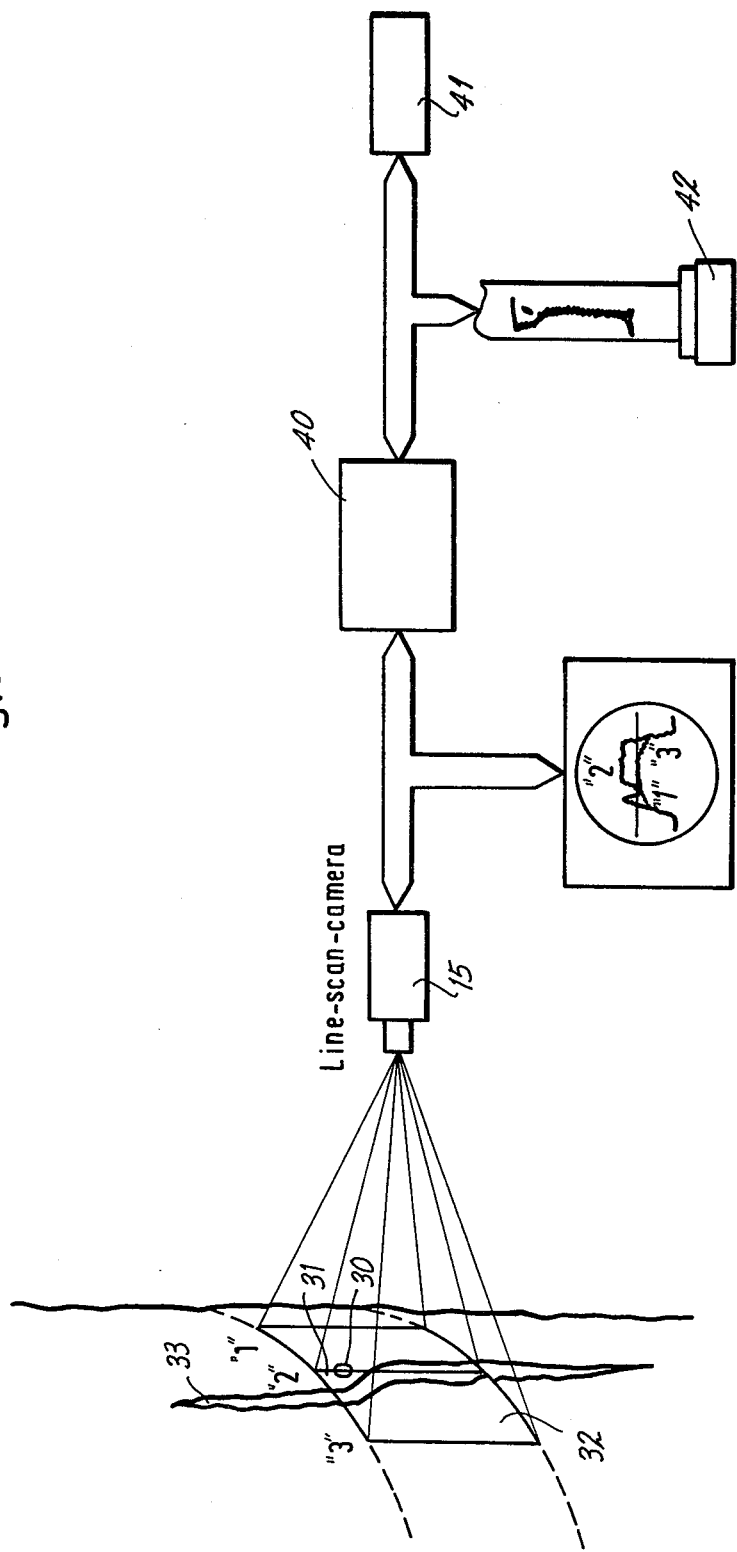
FIG. 3 is a schematic illustration of the inspection and evaluation process as applied to a round casting under utilization of the device shown in FIG. 2.

FIG. 3 illustrates a scanning spot 30 which is, in fact, the particular incremental area observed by the one diode in camera 15, being interrogated internally in that instant. The vertical line scan "moves" that spot 30 along a vertical line 31, and upon rotation of the camera, the scanning band 32 results.

The camera may be connected to an oscilloscope, in which one line of scanning is displayed over the horizontal, the vertical being the amplitude of the radiation received and detected. Three different, spaced-apart scanning strips "1", "2", and "3" are depicted on the casting 3 (the spot 30 is on strip "2" (=31) in this instant. The image intensity for the strips "1" and "3" will be approximately the same; but due to surface crack 33, strip "2" exhibits a different pattern of emanated radiation.

The line scan and input signals of the camera may also be fed, in digitized form, to a processor 40 which may control an alarm device 41 if a defect is detected. The processor 40 may also control a strip printer 42 on a running basis. In fact then, FIG. 3 shows three versions of monitoring the surface, two serving directly for visual inspection, and the alarm device catches any otherwise undetected surface defects.

Figure 4:
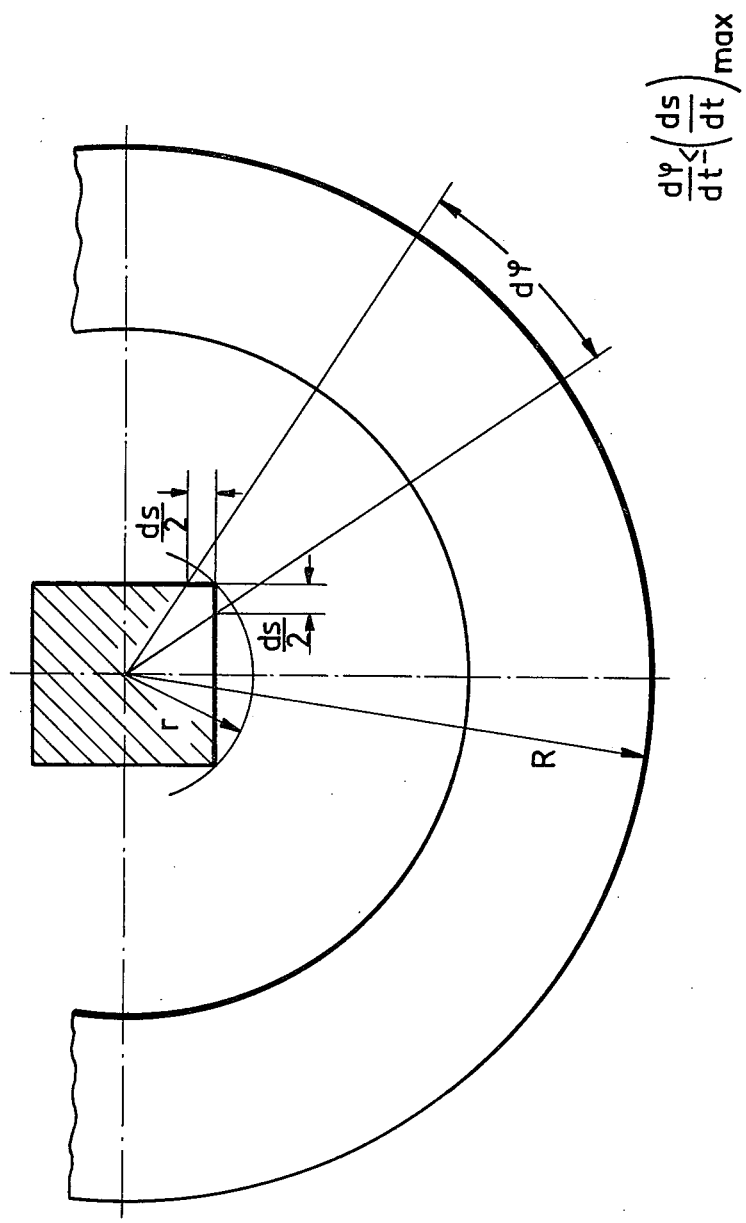
FIG. 4 illustrates, in an elevational view, the application of the same equipment to a casting (in cross section) with square-shaped cross section.

It will be apparent that the regular inspection of the surface of a casting is facilitated when the casting is, indeed, circularly round. The situation is somewhat more complicated when the casting is of quadrilateral cross-sections, e.g., square-shaped as shown in FIG. 4. In order to ensure an adequate resolution, the angular velocity ($d\phi/dt$) of the camera (radius of rotation=R) must be particularly related to the maximum permissable speed of surface scanning $(ds/dt)_{max}$, taken in the direction of rotation. The maximum surface scanning speed is related directly to the radius r, being half the diagonal of the square. The relation is: $d\phi/dt \leq (ds/dt)_{max}$.

Another aspect to be considered is the possibility of a second camera in diagonally opposed disposition. This establishes a redundancy, but serves an additional purpose. In the case of two cameras, their respective scanning lines should be orthogonal to each other, each at an angle of 45° to the axis. This ensures that any defect will at least once be traversed by a scan that runs, more or less, transversely across a boundary to thereby produce a noticeable drop in the radiation received. Defect recognition is easier, in comparison with a situation in which the scan runs, more or less, parallel to such a defect boundary.

The invention is not limited to the embodiments described above; but all changes and modifications thereof, not constituting departures from the spirit and scope of the invention, are intended to be included.

We claim:

1. An apparatus for inspecting the surface of a casting after having emerged from a mold in a machine for continuous casting, the casting moving along on axis, comprising:
    a basically ring-shaped housing arranged concentric to said axis and having an inside wall facing the casting centrally passing through the space surrounded by the ring, the wall having an annular gap;
    a sheet means movably disposed in the housing for closing the gap covering most of the gap, except for a relatively small gap portion and revolving about said axis;
    a line scan camera in the housing connected to the sheet means and revolving therewith about said axis, the camera oriented in such a way so that the lines of the scan extend parallel to the axis so that a narrow increment on the casting is inspected for each line scan.

2. An apparatus as in claim 1, the housing being made of two parts, each part having separate cooling systems.

3. An apparatus as in claim 2, one part having a U-shaped cross sections.

4. An apparatus for inspecting the surface of a casting after having emerged from a mold in a machine for continuous casting, the casting moving along an axis, comprising:
    means defining an enclosure for surrounding the casting, and having a gap facing the casting;
    means for closing the gap but being capable of revolving in the enclosure so that a relatively narrow gap in the means remains for closing which revolves about said casting;
    a line scan means connected to the means for closing, revolving therewith, and observing the casting through the narrow gap for incrementally scanning observable surface portions of the casting, whereby the line scan runs along the axis and is expanded upon revolving of the line scan means; and
    means in the enclosure for driving the means for closing and the line scan means for obtaining said revolving.

5. An apparatus as in claim 1 or 4, including means for controlling the means for driving so that a helical scanning band with overlapping loops is obtained on the casting.

6. An apparatus as in claim 4, the means defining an enclosure including water-cooling means.

7. An apparatus as in claim 6, there being lamella means, extending from an outer wall of the enclosure into the vicinity of a path for the revolving line scan means.

8. An apparatus as in claim 1, the camera running on a track in the housing by means of rotating ball connections.

9. An apparatus as in claim 1 or 3, the housing or enclosure being comprised, at least in part, by a welded-together cooling tubing.

10. A method of inspecting a casting emerging from a mold for continuous casting, comprising the steps of
    line-scanning the surface of the casting axially, by means of a revolving camera, revolving about the emerging casting; and
    shielding the camera from the casting, except for a narrow inspection gap through which that camera observes the casting at any instant.

11. A method as in claim 10, including additionally inspecting the casting by line scanning from a diametrically opposite position.

12. A method as in claim 11, wherein the line scanning and the additional line scanning are carried out in orthogonal directions.

* * * * *